United States Patent
Bromberg et al.

(10) Patent No.: US 9,400,297 B2
(45) Date of Patent: *Jul. 26, 2016

(54) SYSTEM AND METHOD FOR MEASURING RETENTATE IN FILTERS

(71) Applicant: Filter Sensing Technologies, Inc., Cambridge, MA (US)

(72) Inventors: Leslie Bromberg, Sharon, MA (US); Alexander Sappok, Cambridge, MA (US); Ronald Parker, Belmont, MA (US); Peter Koert, Boston, MA (US)

(73) Assignee: CTS Corporation, Elkhart, IL (US)

( * ) Notice: Subject to any disclaimer, the term of this patent is extended or adjusted under 35 U.S.C. 154(b) by 312 days.

This patent is subject to a terminal disclaimer.

(21) Appl. No.: 13/743,691

(22) Filed: Jan. 17, 2013

(65) Prior Publication Data

US 2013/0127478 A1    May 23, 2013

Related U.S. Application Data

(63) Continuation of application No. 12/609,402, filed on Oct. 30, 2009, now Pat. No. 8,384,396, and a continuation-in-part of application No. 11/741,832, filed on Apr. 30, 2007, now Pat. No. 7,679,374.

(60) Provisional application No. 61/110,965, filed on Nov. 3, 2008, provisional application No. 60/746,081, filed on May 1, 2006.

(51) Int. Cl.
*G01R 27/04* (2006.01)
*B01D 46/00* (2006.01)
*F01N 9/00* (2006.01)

(52) U.S. Cl.
CPC ............ *G01R 27/04* (2013.01); *B01D 46/0086* (2013.01); *F01N 9/002* (2013.01);
(Continued)

(58) Field of Classification Search
CPC . B01D 46/0086; F01N 9/002; F01N 2370/22; F01N 2550/04; F01N 2560/14; F01N 2900/1606; F01N 2900/1611; F01N 2560/12; G01R 27/04; Y02T 10/47
See application file for complete search history.

(56) References Cited

U.S. PATENT DOCUMENTS 4,024,452 A    5/1977  Seidel
4,042,879 A    8/1977  Ho et al.
(Continued)

FOREIGN PATENT DOCUMENTS

CN        1032238 A     4/1989
CN      101078692 A    11/2007
(Continued)

OTHER PUBLICATIONS

European Search Report mailed Jun. 11, 2013 in co-pending European patent application No. 07761557.3 (MIT—12205—Europe).
(Continued)

*Primary Examiner* — Benjamin M Baldridge
(74) *Attorney, Agent, or Firm* — Daniel Deneufbourg

(57) ABSTRACT

A system and method for determining loading of a filter having a first dielectric constant with a material having a different dielectric constant, is disclosed. The filter is contained within a metallic container forming a microwave cavity, and microwave or RF energy is created within the cavity and changes in the cavity microwave response are monitored. The changes in cavity microwave response are related to filter loading. In a preferred embodiment, the microwave energy includes multiple cavity modes thereby allowing determination of spatial distribution of the contaminant material loading. In one embodiment, the microwave cavity response includes a shift in frequency of a resonant mode. Alternatively, the microwave cavity response includes a shift in quality factor Q of a resonant mode. The microwave cavity response may include a shift in amplitude or peak width of the microwave's signal at resonance.

20 Claims, 13 Drawing Sheets

(52) U.S. Cl.
CPC ......... *F01N2370/22* (2013.01); *F01N 2550/04* (2013.01); *F01N 2560/12* (2013.01); *F01N 2560/14* (2013.01); *F01N 2900/1606* (2013.01); *F01N 2900/1611* (2013.01); *Y02T 10/47* (2013.01)

(56) References Cited

U.S. PATENT DOCUMENTS

| | | | |
|---|---|---|---|
| 4,477,771 A * | 10/1984 | Nagy et al. | 324/636 |
| 4,689,553 A | 8/1987 | Haddox | |
| 5,074,112 A | 12/1991 | Walton et al. | |
| 5,142,595 A | 8/1992 | Chester | |
| 5,157,340 A * | 10/1992 | Walton et al. | 324/641 |
| 5,369,369 A | 11/1994 | Cutmore | |
| 5,423,180 A | 6/1995 | Nobue et al. | |
| 5,497,099 A | 3/1996 | Walton | |
| 5,500,599 A | 3/1996 | Stange | |
| 6,131,386 A * | 10/2000 | Trumble | 60/274 |
| 6,147,503 A | 11/2000 | Nelson et al. | |
| 6,507,308 B1 | 1/2003 | Ono et al. | |
| 6,819,849 B1 | 11/2004 | Tangonan et al. | |
| 6,854,261 B2 | 2/2005 | Williamson et al. | |
| 7,157,919 B1 | 1/2007 | Walton | |
| 7,357,822 B2 | 4/2008 | Hamahata et al. | |
| 7,679,374 B2 | 3/2010 | Bromberg et al. | |
| 8,384,396 B2 | 2/2013 | Bromberg et al. | |
| 8,384,397 B2 | 2/2013 | Bromberg et al. | |
| 8,889,221 B2 | 11/2014 | Sappok et al. | |
| 9,144,831 B2 | 9/2015 | Sappok et al. | |
| 2001/0003898 A1 | 6/2001 | Miller et al. | |
| 2001/0007571 A1 | 7/2001 | Murphy et al. | |
| 2004/0200198 A1* | 10/2004 | Inoue et al. | 55/282.3 |
| 2006/0027511 A1* | 2/2006 | Brown et al. | 210/793 |
| 2006/0070373 A1 | 4/2006 | Huang et al. | |
| 2006/0101793 A1* | 5/2006 | Gregoire et al. | 55/282.3 |
| 2006/0229466 A1 | 10/2006 | Arhancet et al. | |
| 2007/0000218 A1 | 1/2007 | Wirth et al. | |
| 2007/0056274 A1* | 3/2007 | Wills | 60/297 |
| 2007/0068157 A1 | 3/2007 | Kurtz | |
| 2007/0125075 A1 | 6/2007 | Zanini-Fisher et al. | |
| 2007/0125349 A1 | 6/2007 | Zanini-Fisher et al. | |
| 2007/0130923 A1 | 6/2007 | Dye et al. | |
| 2007/0209333 A1* | 9/2007 | Kondou | 55/282.3 |
| 2007/0214862 A1 | 9/2007 | Kubinski et al. | |
| 2008/0059093 A1 | 3/2008 | Bromberg et al. | |
| 2008/0066621 A1 | 3/2008 | Naito et al. | |
| 2008/0092499 A1 | 4/2008 | Otsuka et al. | |
| 2008/0110143 A1* | 5/2008 | Chen et al. | 55/385.1 |
| 2008/0264036 A1* | 10/2008 | Bellovary | 60/274 |
| 2009/0038294 A1* | 2/2009 | Anderson et al. | 60/295 |
| 2010/0101409 A1 | 4/2010 | Bromberg et al. | |
| 2010/0102828 A1 | 4/2010 | Bromberg et al. | |
| 2012/0138093 A1 | 6/2012 | Sappok et al. | |
| 2013/0125745 A1 | 5/2013 | Bromberg et al. | |
| 2014/0116028 A1 | 5/2014 | Sappok et al. | |

FOREIGN PATENT DOCUMENTS

| | | |
|---|---|---|
| EP | 0356040 A2 | 2/1990 |
| JP | 4-505665 A | 10/1992 |
| WO | 92/02807 A1 | 2/1992 |
| WO | 93/05388 A1 | 3/1993 |
| WO | 00/50743 A1 | 8/2000 |
| WO | 2004/074670 A2 | 9/2004 |
| WO | 2005/093233 A1 | 10/2005 |
| WO | 2006/002037 A2 | 1/2006 |
| WO | 2007/130896 A2 | 11/2007 |

OTHER PUBLICATIONS

International Search Report/Written Opinion mailed Dec. 23, 2009 in co-pending PCT application No. PCT/US2009/062757.

International Preliminary Report on Patentability mailed May 12, 2011 in co-pending PCT application No. PCT/US2009/062757.

International Search Report/Written Opinion mailed Dec. 23, 2009 in corresponding PCT application No. PCT/US2009/062782.

International Preliminary Report on Patentability mailed May 12, 2011 in corresponding PCT application No. PCT/US2009/062782.

Chinese Communication, with English translation, issued Dec. 5, 2012 in corresponding Chinese patent application No. 200980143806.3.

International Search Report/Written Opinion mailed Feb. 19, 2008 in co-pending PCT application PCT/US07/67750.

International Preliminary Report on Patentability issued Nov. 4, 2008 in co-pending PCT application No. PCT/US2007/067750.

Office Action mailed Mar. 10, 2015 in co-pending U.S. Appl. No. 13/743,712.

Notice of Allowance mailed Oct. 14, 2015 in co-pending U.S. Appl. No. 13/743,712.

\* cited by examiner

SYSTEM AND METHOD FOR MEASURING RETENTATE IN FILTERS

This application is a continuation of U.S. patent application Ser. No. 12/609,402, filed Oct. 30, 2009, which is a continuation-in-part of U.S. patent application Ser. No. 11/741,832 filed Apr. 30, 2007 (Now U.S. Pat. No. 7,679,374 issued Mar. 16, 2010), which claims the benefit of U.S. Provisional Patent Application 60/746,081, filed May 1, 2006, the disclosures of which are herein incorporated by reference in their entireties.

This application claims the benefit of U.S. Provisional Patent Application Ser. No. 61/110,965, filed Nov. 3, 2008, the disclosure of which is herein incorporated by reference in its entirety.

BACKGROUND

This invention relates to determination of contaminant material loading on a filter and more particularly to the use of radio frequencies to determine loading.

In many realms, there is a need for accurate sensing of the amount of material that has been captured by a filter. An example is the need to determine loading of air filters in HVAC systems, filter bag houses used in industrial applications, and even filters used with liquids, and the like.

Yet another example is the need to determine filter loading of soot on a particulate filter. The amount of loading on a particulate filter must be known in order to determine appropriate conditions for start-up of regeneration as well as monitoring conditions to determine when complete regeneration has been achieved. The level of loading is important in this context because regeneration of a particulate filter is often through an uncontrolled burn in which soot is ignited by the presence of free oxygen and a combustion wave is generated through the filter. Under certain conditions, it is possible that regeneration will produce temperatures that are very high, resulting in large thermal stresses that can result in limited fatigue life of the filter and ultimately, its destruction. Thus, the level of soot loading is important for successful filter regeneration.

A specific application of a particulate filter is a diesel particulate filter (DPF). Currently, filter pressure drop measurements are used to estimate the amount of soot accumulated in the DPF. In some cases, predictive models may also be used to estimate filter soot loading. Pressure drop measurements alone provide only an indirect and imprecise measure of soot accumulation in the particulate filter, and suffer from a number of disadvantages. Exhaust gas composition, temperature, and flow rates all affect filter pressure drop and must be accounted for to accurately relate pressure drop to filter soot loading. Further, the spatial distribution of the accumulated ash and soot also affects the pressure drop measurement, and this distribution may change with time, particularly as the filter becomes loaded with ash.

Following repeated regenerations, a substantial amount of ash may also accumulate in the particulate filter. Pressure drop measurements are unable to distinguish between soot and ash accumulation in the filter, the latter of which introduces additional error in soot load estimates based on pressure drop. Additionally, many types of filters exhibit a non-linear pressure drop response and pressure drop hysterisis depending upon the loading state and history of the filter, which further complicates pressure-based filter load measurements.

Pressure drop-based estimates of soot accumulation in the DPF are also characterized by generally slow response times and low sensitivities to small changes in soot load. Further, the inability of these systems to directly monitor ash levels in the filter requires the filters to be periodically inspected, resulting in vehicle or machine down-time, regardless of the actual filter ash level. Additionally, pressure-drop based measurements are unable to detect all but the most catastrophic of filter failures, and, in most cases, can not meet stringent on-board diagnostic requirements.

In order to address some of the shortcomings inherent to filter pressure drop measurements, various predictive models are generally used in conjunction with these measurements. While various types of models exist, many utilize a number of engine operating parameters, inputs from various engine and exhaust sensors, and the time between regeneration events, to predict the amount of soot accumulated in the DPF. In many cases, these models are uploaded in the engine control unit (ECU). These models are generally calibrated for a specific engine and fuel, requiring recalibration for each specific application. Furthermore, when used with cleaner burning fuels, (compared to the fuel with which the models were initially calibrated) the models tend to over-predict filter soot loading, resulting in unnecessary filter regenerations and fuel economy penalties. The combined use of predictive models and filter pressure drop measurements does little to overcome the deficiencies listed above. These shortcomings lead to inefficient system operation, fuel economy penalties, increased filter thermal cycling and fatigue, and reduced filter service life.

Exhaust gas soot sensors have also been proposed to measure the concentration of soot aerosols directly in the exhaust gas entering the particulate filter. These measurement systems suffer from the deficiency that the amount of soot accumulated on the particulate filter is not necessary equivalent to the amount of soot entering the filter, as some level of passive regeneration may take place, depending on exhaust conditions. Further, exhaust gas soot sensors provide no information on ash accumulation or soot and ash distribution in the DPF. In addition, many of these sensors suffer from soot fouling, consume excessive amounts of energy, and are subject to error introduced by exhaust temperature, exhaust gas velocity, and other factors.

Radio frequency (RF)-based particulate load monitoring systems have also been proposed. One such system monitors filter loading and initiates filter regeneration based on the magnitude of a low-frequency (RF) signal transmitted through the filter. This system, by restricting use to low frequencies below those required to establish resonance in a cavity, overlooks many of the advantages to utilizing higher frequencies required to generate multiple cavity resonant modes.

The use of microwaves to detect soot content in a particulate trap was also proposed. One such system detects soot content in a particulate filter by monitoring a change in filter resonant frequency. However, such systems cannot determine the spatial distribution of soot content within the particulate filter.

All RF and microwave filter load monitoring systems heretofore known suffer from a number of disadvantages:

(a) Prior Art systems are unable to monitor the spatial distribution of material accumulated in the filter. Ash accumulation in the filter displaces soot and alters its distribution. Further, non-uniform flow conditions may also result in non-uniform material accumulation.

(b) All known filter load monitoring systems initiate filter regeneration based on some average total filter soot load. Locally high soot loads cannot be detected by systems which are not capable of measuring material distribution in the filter.

(c) Previous microwave- and RF-based filter loading systems cannot simultaneously detect both soot and ash accumulation in the filter over all exhaust conditions.

(d) These systems do not detect filter failures or malfunctions, which is important to ensure the filter is operating as required.

(e) These systems do not detect malfunctions or failures of individual components, such as sensors, for example, that may be required for correct operation of the filter.

(f) Microwave and RF-based measurement systems are affected by moisture content and water vapor present in the exhaust gas and on the filter, which must be accounted for to reduce error in the measurement.

(g) Previous filter load monitoring systems fail to communicate with existing engine and exhaust sensors to provide feedback control capabilities useful to modify engine operation to optimize the combined engine and after-treatment system performance.

Therefore, it would be beneficial if there were a filter load measurement system that addressed the problems described above. Such a system would be advantageous in that lower emission limits may be achieved, while minimizing the amount of maintenance and unnecessary regeneration cycles. In addition, the use of multiple resonance modes would allow more detailed estimation of the special loading within the device.

In addition to particulate filters, the same filter load measurement system could be applied to a wide range of filters, including fiber filters, various porous media used for filtration, and the like. One example is air filters used in HVAC systems, where determination of the state of filter loading is important to determine when to clean or replace the filter. Similarly, bag-type filters are often cleaned by reverse flow and determining when to clean the filters based on the state of filter loading is also important.

SUMMARY

A system and method for determining loading of a filter having a first dielectric constant with a material having a different dielectric constant, is disclosed. The filter is contained within a metallic container forming a microwave cavity, and microwave or RF energy is created within the cavity and changes in the cavity microwave response are monitored. The changes in cavity microwave response are related to filter loading. In a preferred embodiment, the microwave energy includes multiple cavity modes thereby allowing determination of spatial distribution of the contaminant material loading.

In one embodiment, the microwave cavity response includes a shift in frequency of a resonant mode. Alternatively, the microwave cavity response includes a shift in quality factor Q of a resonant mode. The microwave cavity response may include a shift in amplitude or peak width of the microwave's signal at resonance.

At least one antenna may be used to transmit/receive microwave energy. In one embodiment, one antenna only is used in a reflection mode to transmit/receive the microwave energy. Two antennas may be used in a transmission mode with one antenna transmitting and the other antenna receiving. Instead of an antenna, at least one waveguide may be used to transmit/receive the microwave energy. In an embodiment, one waveguide is used in reflection mode to transmit/receive the microwave energy. Alternatively, two waveguides may be used in transmission mode with one waveguide transmitting and the other wave guide receiving.

In another embodiment, the filter is a diesel particulate trap for removing particulate matter from the exhaust of a diesel engine. The particulate matter may be soot. It should be noted that the filter may be any filter and the particulate matter may be any contaminant material collected on the filter.

In still another embodiment, the metallic container includes a cylindrical portion between two transition cones, one of which is connected to an exhaust pipe. The microwave energy may be in the S-band, although any range of frequencies may be used. Suitable materials include cordierite and silicon carbide, among others. Both low order and high order cavity modes may be used to monitor filter loading. In this embodiment, the frequency of operation may be chosen so that the modes are operating at cutoff at small inlet and outlet regions of the filter.

When two antennas or waveguides are used, they may be located on opposite sides of the filter or on the same side of the filter. In one embodiment, the antennas and waveguides may be located on the downstream side of the filter to prevent contamination.

The microwave energy may be provided by a modified microwave chip and the microwave energy may be monitored by a diode with or without amplification. Cavity monitoring may use lock-in detection and/or homodyne detection, or heterodyne detection.

DETAILED DESCRIPTION

Figure 1:
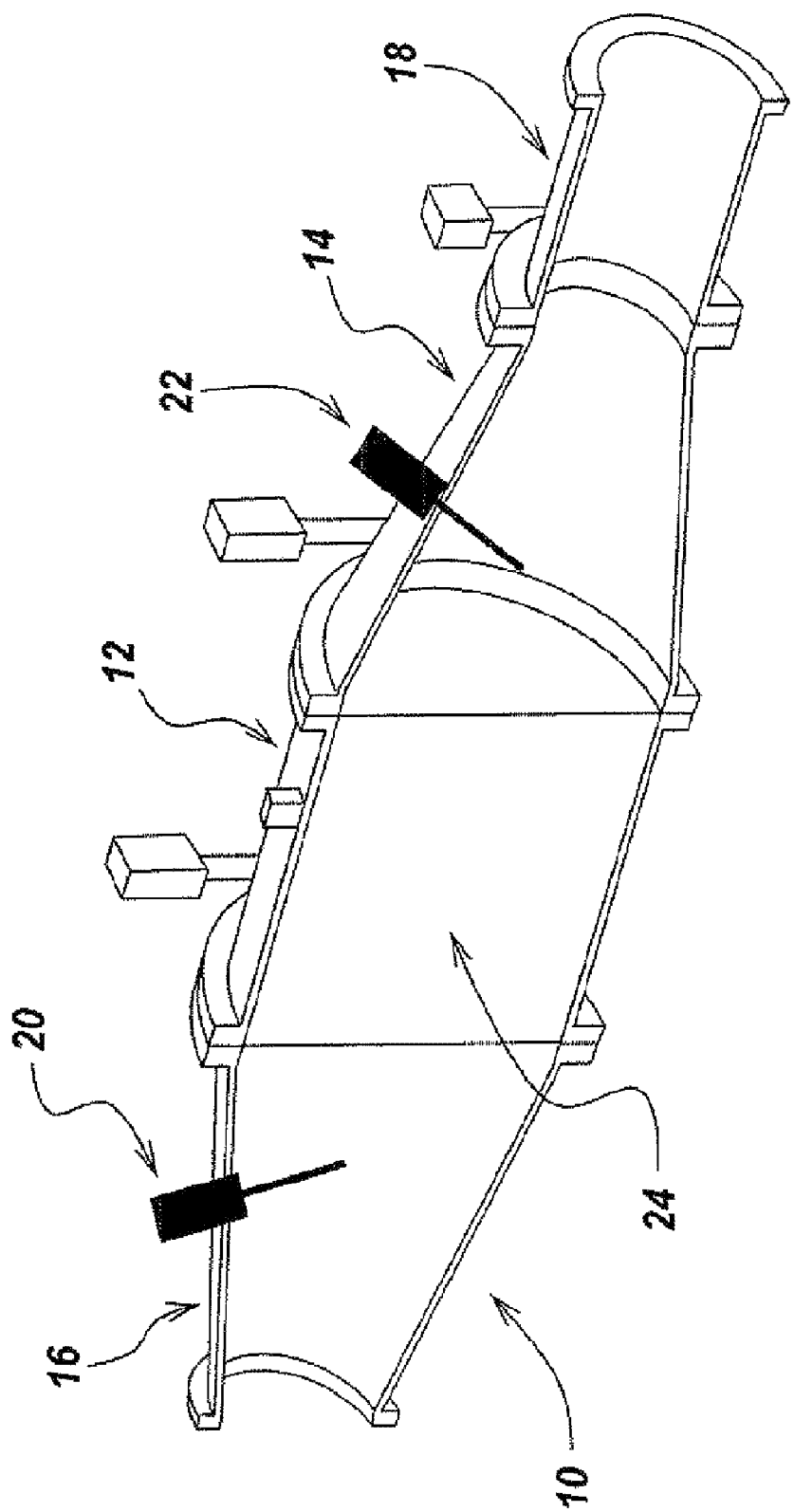
FIG. 1 is a perspective view of a canned diesel particulate filter according to an embodiment of the invention.

The present invention is based on the recognition that microwaves can be used to determine the status of loading of traps or filters. The loading may be soot, particulates, ash or any solid/liquid. In addition to determining the total amount of loading, the microwave system to be described herein is useful in determining the distribution of the loading throughout the filter. The microwave sensing used in this invention can be inexpensive, as inexpensive oscillators and detectors in the frequency range of interest are commercially available.

In the case of a diesel particulate filter, the particulates are made from soot and other organic compounds (solid and/or liquid), and ash. For the purposes of this disclosure, the combination of carbon and organic compounds and will be referred to, for simplicity, as soot. Those of skill in the art will recognize that soot and organic compounds are removed through regeneration but ash loading will remain.

In addition, although this disclosure refers to a diesel particulate filter, it should be noted that the filter can be any type of filter. Further, the material loading of the filter need not be soot or ash but may be any material with dielectric properties that differ from the medium it displaces.

In one embodiment, diesel particulate filter units are made of cordierite having a dielectric constant slightly higher than 4, at frequencies around S-band. This material has a small temperature dependence. The presence of soot (which in some cases can be as much as 10 g/liter of trap, with the size of the trap being about two liters for 5.66 inch traps) changes the microwave characteristics of the microwave cavity. Thus, the maximum soot loading for this trap could be as high as 20 g with a volume of about 20 $cm^3$. This amount of soot corresponds to a substantial volume and a correspondingly large change in the dielectric characteristics of the trap. It is noted that the dielectric constant of soot is approximately 2.

Silicon carbide is also suitable for the manufacture of a diesel particulate filter. The microwave properties of silicon carbide also make it suitable for the use of microwaves for loading sensing. Those skilled in the art will recognize that the microwave load sensing technology disclosed herein can be used, for example, to determine the loading of fiber filters (organic and inorganic fibers), such as those used in baghouses, and in other applications where substantial masses/volumes of materials that have non-unity dielectric constants are collected.

In addition, although the term "microwave" is used throughout this disclosure, it is noted that the methods and apparatus disclosed herein may be equally applicable to energy at other frequency ranges. For example, energy in the RF range may also be used to test for loading.

Ash content, which is not removed through regeneration, can be monitored if substantial ash amounts build with time on the trap.

Low order cavity modes as well as high order modes can be used to monitor the trap loading and spatial distribution of the collected material. Different cavity modes have different electric field patterns with peaks and nulls that vary across the volume. For a given cavity mode, only the presence of soot in those regions with high electric field affects the microwave response in the cavity. By choosing different modes in the cavity, it is possible to sample different regions and thus obtain information on the soot distribution.

The presence of soot affects the cavity response in several ways. The resonant frequency shifts to lower frequencies with soot buildup. In addition, the cavity quality Q is affected by the presence of absorbing soot. Further, the amplitude of the signal at resonance decreases with soot buildup. All three of these parameters can be used to determine the soot level. Several modes can be used to monitor the loading in various regions of the diesel particulate filter.

The invention will now be described in conjunction with the figures. With reference first to FIG. 1, a diesel particulate filter unit 10 includes a metallic cylinder portion 12 and transition cones 14 and 16. The cone 14 connects to an exhaust pipe 18. In this embodiment, a pair of rod antennas 20 and 22 are located on opposite sides of a filter 24.

Because of the conical transition sections 14 and 16, the frequency of operation can be chosen so that the modes are operating at cutoff at the small inlet and outlet regions of the trap, with the frequency such that the modes are operating below cutoff on main exhaust pipe 18. It is not necessary to provide screens to confine the microwave radiation.

In the embodiment of FIG. 1, one of the conventional rod antennas, 20 and 22, serves as a transmitter and the other serves as a receiver. It should be understood that both of the rod antennas 20 and 22 could be located on the same side of the filter 24 rather than flanking it. In this case, the preferred location for the rod antennas 20 and 22 will be downstream from the filter element 24 to minimize soot on the surface of the transmitter, receiver or associated components.

Figure 2:
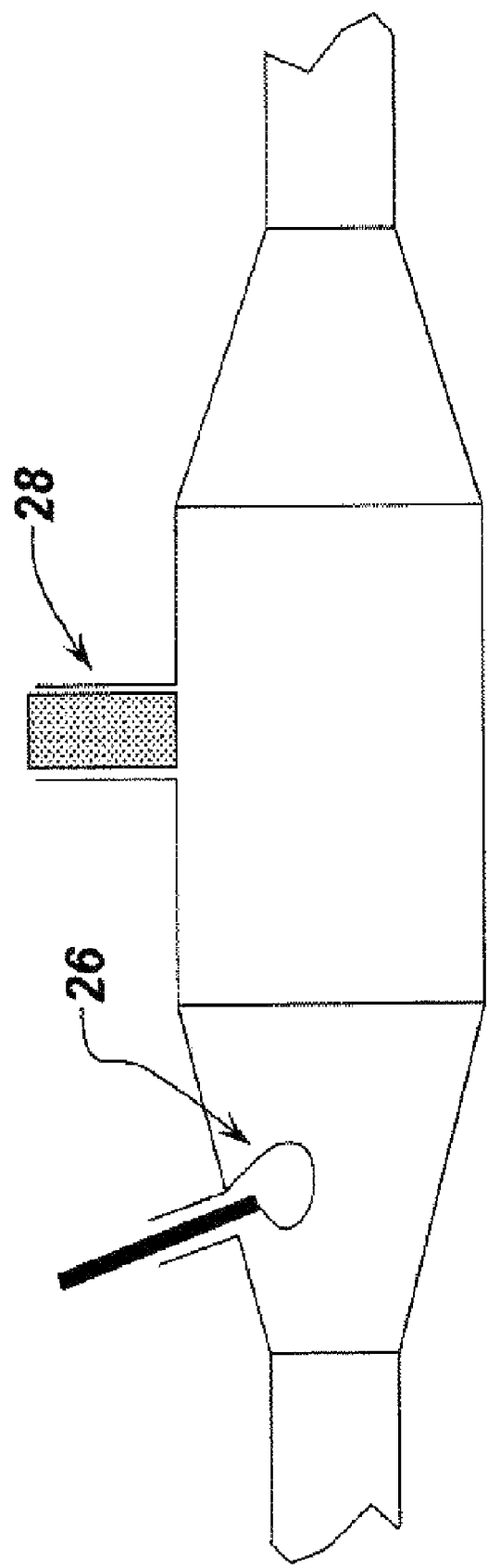
FIG. 2 is a cross-sectional view of another embodiment of the invention.

With reference now to FIG. 2, it is possible to implement the transmitter through the use of a loop antenna 26, or through the use of a waveguide 28. The waveguide 28 may be filled with a high dielectric material. It is also contemplated to use the loop antenna 26 and/or the waveguide 28 to monitor the radiation by acting as receiving antennas.

It is possible to use a single antenna (rod or loop), as well as a single waveguide, or to use two antennas or waveguides. In the case of a single antenna/waveguide, the information is in the reflected signal. In the case of separate antennas/waveguides for transmitter/receiver, it is possible to choose between reflection or transmission modes. In the case of two antennas/waveguides, there are four elements in the coupling matrix that could be used to determine soot loading: transmission from one antenna/waveguide to the other, the reverse, and reflection in each antenna/waveguide.

As shown in FIG. 2, one suitable location of the transmitter and/or receiver is in the central region of the filter 24. This location illustrates a clear advantage of the microwave system disclosed herein as the waves penetrate through the external surface of the filter 24 and a sensor can thus be protected from soot deposition by the external walls of the filter 24. This arrangement can be done for either single or double waveguides, loop antennas or rod antennas.

Figure 3:
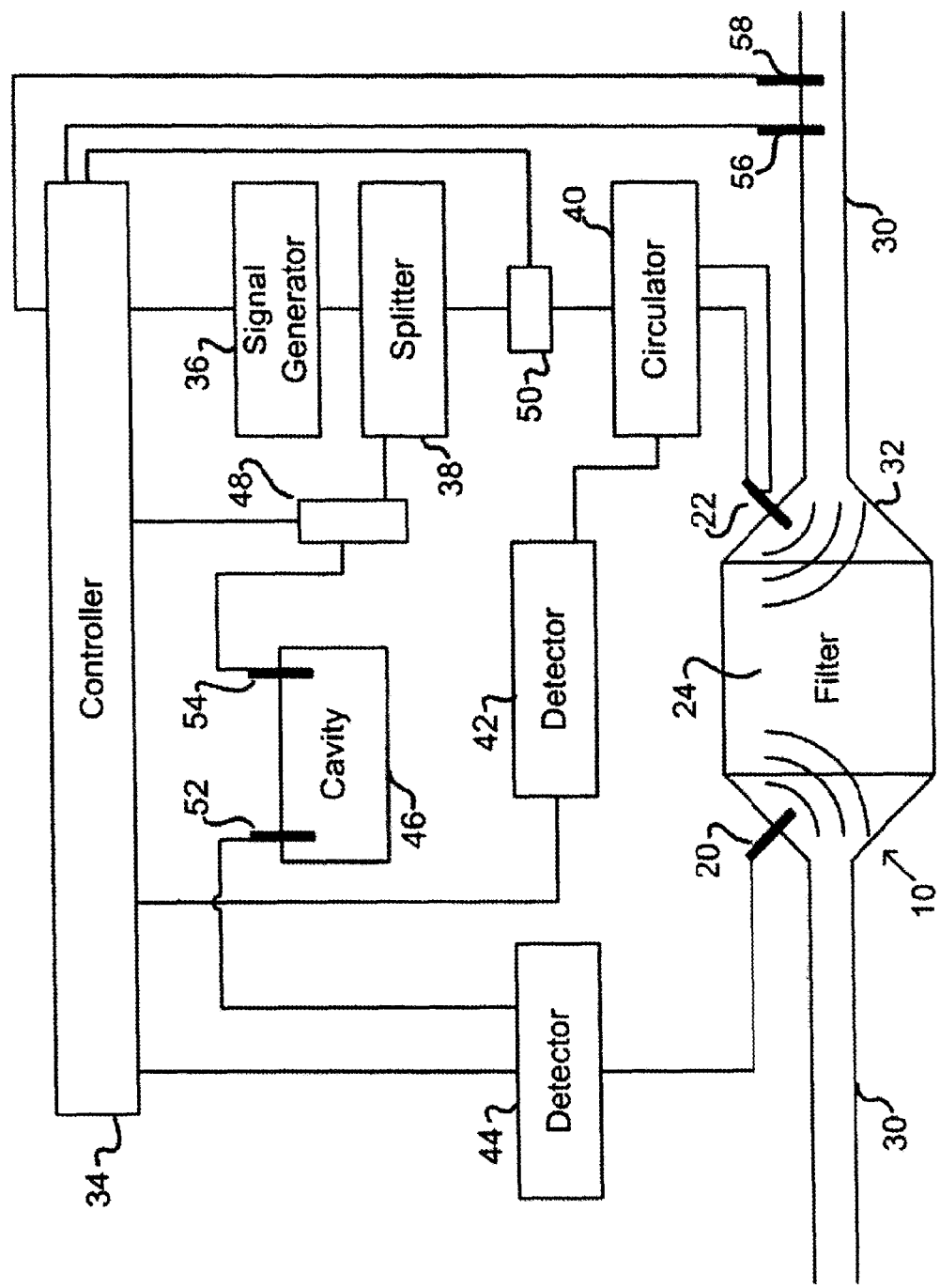
FIG. 3 is an illustration of a microwave filter measurement system according to one embodiment.

One embodiment of the system for transmitting and receiving microwave energy through the filter 24 and processing the received signal is shown in FIG. 3. The filter 24 is contained within a filter housing 32 forming a microwave resonant cavity, constituting the particulate filter unit 10. The housing 32 may be designed in such a way as to optimize its resonance properties. The housing 32 may be connected to a conduit 30 to direct a flow through the filter 24. One or more probes 20 and 22 may be mounted to the housing 32 to transmit and receive microwave energy.

Meshes or screens (not shown) may or may not be attached to conduit 30 or housing 32 to confine the microwave energy. In some applications, the use of high frequencies may be desired requiring the use of meshes, screens, or some other form of restriction of the conduit 30 to confine the microwave energy and create a resonant cavity at these conditions.

In one embodiment, the microwave filter sensing system, shown in FIG. 3, may include a controller 34. The controller 34 may be integrated into an existing control unit, such as an engine control unit (ECU), or be a stand alone control unit, and may or may not communicate with other control systems. There may be one or more controllers 34. The controller may control a signal generator 36 configured to produce microwave signals over a given frequency range. In one example, the signal generator 36 may be a voltage controlled oscillator and the controller 34 may be configured to control the signal generator 36 by means of a variable voltage.

The controller 34 may be a processing unit, such as a microprocessor or custom semiconductor device, which is configured to execute a set of instructions. These instructions can be programmed into the device permanently, or may be stored in a readable storage element, such as a memory device. The memory may be read-only, such as a ROM, or may be rewritable, such as RAM, DRAM, FRAM, or a combination of the two. In addition to memory, the controller 34 may have input and output ports so that it can communicate with the various sensors, detectors and other devices described herein.

The microwave signal produced by signal generator 36 may be fed into a splitter 38 and to a circulator 40. The circulator may be connected to probe 22 that may be configured to transmit and receive microwave signals in cavity 32. The circulator may further be connected to detector 42, and detector 42 may be connected to controller 34. In one embodiment, detector 42 may be a diode detector, such as a Schottky diode, for example, configured to detect microwave signals received by probe 22.

The controller 34 may be connected to a detector 44 configured to detect microwave signals from probe 20. Detector 44 may be a diode detector in one embodiment, such as a Schottky diode. Other detectors are also possible. Detector 44 may further be connected to a probe 52 mounted in cavity 46. Another probe 54 may also be mounted in cavity 46 and connected to splitter 38 by means of switch 48. Switches 48 and 50 may also be connected to controller 34. Controller 34 may be configured to close switch 50 and open switch 48 to allow a signal to pass from splitter 38 to circulator 40 in order to introduce microwave energy in cavity 32 to monitor filter 24 loading. In another mode of operation, controller 34 may close switch 48 and open switch 50 to transmit a signal from splitter 38 to probe 54. Transmitting a signal from probe 54 through cavity 46 to probe 52 may be useful to perform a self diagnostic function to determine if the microwave filter sensing system shown in FIG. 3 is functioning properly. In this embodiment, cavity 46 may serve as a reference cavity and may or may not contain any openings.

It should be noted that the system shown in FIG. 3 may not require the use of cavity 46, probes 52 and 54, or switches 50 and 48, which provide additional self-diagnostic functionality, if this functionality is not required in certain applications.

The microwave filter sensing system may also include a temperature sensor 56 and a moisture sensor 58. Sensors 56 and 58 may be mounted at any location along conduit 30 on housing 32 or in filter 24. The microwave measurement may be affected by variations in temperature or moisture content in the resonant cavity 32. Sensors 56 and 58 may allow for controller 34 to modify the microwave signal by performing a temperature or moisture compensation.

In operation, microwave energy is established within the cavity 32 of the device 10. There are a large number of modes that can be used to determine the trap loading. In one embodiment, signal generator 36 may be configured to generate a radio-frequency signal and sweep a frequency range sufficient to generate more than one cavity resonant mode in housing 32. In another embodiment, signal generator 36 may be configured to only sweep the frequency ranges required to generate the desired resonant modes. The required frequency range is a function of the cavity 32 size. In one example, the cavity 32 may have a diameter of 5.66 inches and a length of 6 inches and the frequency range of operation may be from 1 GHz to 2 GHz. However, any cavity 32 size and frequency range may be used. The frequencies may or may not be in the microwave range, depending upon the cavity 32 size and geometry.

In one embodiment, controller 34 may control signal generator 36 to generate a microwave signal sufficient to produce more than one resonant mode in cavity 32. Splitter 38 may direct the microwave signal to circulator 40. Switch 50 may or may not be used. When operating in transmission mode, circulator 40 may direct the microwave signal to probe 22. Probe 22 may transmit the microwave signal from probe 22 through filter 24 to be received by probe 20. Detector 44 may detect the signal received by probe 20 and relay the signal to controller 34. In this manner, the cavity 32 resonance curves may be sampled using transmission.

Operating in reflection mode, circulator 40 may permit probe 22 to transmit and receive the microwave signal. The signal thus transmitted and received by probe 22 may be directed to detector 42. Detector 42 may relay the detected signal to controller 34, thus permitting the cavity 32 resonance curves to be sampled using reflection.

The signal received by detectors 42 or 44 may or may not be filtered or amplified before being sent to controller 34.

Controller 34 may acquire the signal from detectors 44 and 42 and process the signal using analog means, or using a computer program following a set of instructions contained on a computer readable storage medium contained within or accessible by controller 34. Signal processing may include filtering, smoothing, applying correction factors or compensation, such as for temperature, moisture, or composition of the accumulated material, and the computation of various signal parameters and statistics. The controller may carry out temperature or moisture compensation by monitoring temperature sensor 56 or moisture sensor 58 and applying reference values, such as from a look-up table, or a correction function, such as an equation or series of equations. In applications where moisture or temperature compensation is not required, probes 56 or 58 may not be used.

The signal parameters of interest may be the amplitude, frequency, peak width, or quality factor of one or more cavity 32 resonant modes. Controller 34 may sample the entire resonance curve to determine the signal parameters listed above, or only the frequency ranges required for the resonant modes of interest. In one embodiment, the signal parameters listed above may be determined from the resonance curves using a computer program following a set of instructions contained on a computer readable storage medium contained within or accessible by controller 34. Parameter statistics such as mean, median, mode and standard deviation of more than one measurement may also be computed in a similar manner. The parameters described above may be related to the amount, type, and distribution of material accumulated in the filter 24.

The controller 34 may compare the received signal parameters to a reference. This reference may be a set of stored values, based on the geometry of the cavity used. In another embodiment, the reference is a previously received signal. In this way, the controller may monitor changes in the parameters over time.

One means of determining signal quality factor may utilize the controller 34 to modify the signal generator 36 operation. If the signal generator 36 is a voltage controlled oscillator (VCO), the driving voltage for the VCO has an AC signal that is superimposed on a DC signal. The DC signal is varied by the controller 34 until the signal response from detector 44 or 42 shows a maximum. The AC signal amplitude is then varied by controller 34 until the amplitude of the response measured by detector 44 or 42 shows the required peak-to-value ratio, which can be adjusted depending on measurement conditions. If a factor of 2 decrease is chosen as that ratio, then the power is down by 3 db from the peak to the valley.

The amplitude of the AC signal determines the value of Q. The relationship is approximately inversely proportional. Thus, the amplitude of the AC signal is nearly proportional to the width of the resonance curve. Measurements have indicated that the soot accumulation for some resonant modes is linearly proportional to the peak width, and thus the amplitude of the AC signal is approximately proportional to the soot level.

Many methods could be used to measure the peak-to-value, including lock-in techniques (phase sensitive detection). The frequency of the AC signal can also be varied or fixed. Frequencies of 0.1 Hz to 100 Hz could be used.

A circuit can be used that locks on the resonant frequency, such as one that has feedback. By providing the correct amplification (and phase) of the signal, and feeding the VCO with it, an analog circuit can be used to determine the resonant frequency.

In addition to changing the frequency of the source, an alternative method of determining the Q relies on changing the resonant frequency of the cavity 32, with a constant frequency source. The change in the resonant frequency of the cavity 32 can be due to change in size or geometry or change in dielectric constant, or a combination of the two. The resonant mode is swept across the narrow, fixed frequency oscillator, and the response measured. It would be possible to calibrate the effector (size, geometry or dielectric constant) to the resulting change in frequency and thus to the Q of the device. The effector that changes the cavity 32 properties can be an actual change in geometry, such as would be possible with a sliding short at a wall of the cavity 32, or displacement of a dielectric or conducting material that moves (through displacement, rotation or other means) from low fields to high fields. The amount of change required is associated with the Q of the signal, and the stability of the signal generator. Thus, if the signal generator has a frequency stability of amount $\Delta f_{generator}$, the effector needs to change the cavity 32 resonant frequency by a factor of $\Delta f_{generator}$. Similarly, if the amount of loading to be measured results in a change in the resonant frequency of $\Delta f_{loading}$, the change in resonant frequency in the cavity 32 needs to be larger than $\Delta f_{loading}$. The change in resonant frequency due to the effector has to be larger than $\Delta f_{generator}$, $\Delta f_{loading}$ and also the change in Q due to the loading, $f * \Delta Q$.

Alternatively, it would be possible to use a broadband signal to drive the cavity 32, with measurement of the response through a frequency range wide enough to determine Q.

In yet another embodiment, Q could be estimated using a hardware filter. For a clean filter 24 with no soot, Q is high, and the width of the resonant mode is very narrow. A suitable filter design could be used to filter out the signal (peak at resonance). As the filter 24 becomes loaded with soot, Q decreases, the peak width increases, and more of the signal passes through the filter, increasing the sensor output voltage. The filter could be designed such that the increase in voltage output corresponds to Q exceeding some threshold value.

The quality factor may also be determined by measuring the decay of the signal inside the microwave cavity 32, after the signal generator 36 is suddenly turned off.

Controller 34 may also be configured to initiate an action based on the amount, type, or distribution of the material accumulated in the filter 24. In one example, the controller 34 may initiate filter 24 regeneration or trigger an alarm once the filter 24 soot load exceeds some threshold value. Filter 24 regeneration may be triggered based on the total amount of soot accumulated in the filter 24 or the local soot load exceeding some threshold value. In another example, the controller 34 may trigger an alarm once filter 24 ash load exceeds some threshold value to alert the operator to clean or replace the filter 24. In another example, the controller 34 may trigger an alarm in response to the detection of a filter 24 failure or malfunction or the detection of a malfunction with the individual sensors and components depicted in FIG. 3.

The controller 34 may also execute a series of instructions contained on a computer readable storage medium, such as a computer program, or algorithm for example. The computer program may be used to estimate the composition of the material accumulated in the filter 24 based on exhaust or engine operating conditions and filter 24 history. The estimates of material composition include soot constituents such as soluble organic material, carbon, and sulfates, as well as ash, in one example. In another example, the computer program may be used to estimate the amount of material accumulated in filter 24 and the calculated filter 24 loading value compared with the measured filter 24 loading value using microwave sensing or some other means, such as pressure measurements.

In one embodiment, controller 34 may perform a self-diagnostic function to ascertain whether or not the various components and subsystems are functioning correctly. In one example, the controller 34 may control signal generator 36 to generate a reference signal. Splitter 38 may direct the microwave signal to switch 48. Controller 34 may operate switch 48 allowing the reference signal to pass from the splitter 38 through reference cavity 46 to detector 44. Controller 34 may compare said reference signal from detector 44 with the known reference value. If the detected signal and reference value deviate by more than an acceptable amount, the controller 34 may trigger an alarm or log a fault indicating an error or malfunction. In a similar manner a reference cavity and switch may also be utilized between splitter 38 and detector 42 as part of a diagnostic system.

In another embodiment, controller 34 may command signal generator 36 to generate a reference signal transmitted through filter 24 by means of probe 22. The reference signal may be received by probe 20 and detector 44 (transmission) or probe 22 and detector 42 (reflection) and routed back to controller 34. The reference signal may or may not be in the microwave range, and may or may not result in the generation of one or more resonance modes within housing 32. Controller 34 may compare said reference signal from detector 44 or 42 with the known reference value, and in this manner also perform a self diagnostic function.

The resonance curves sampled from cavity 32 may be used to monitor the amount, type, and distribution of the material collected in filter 24. In one example, the material collected in filter 24 may be soot or ash. The characteristics of the resonance curves may further be used to determine the state or health of the filter 24, such as to detect cracks or regions where the filter 24 may have melted for example.

Cavity 32 may be optimized to enhance measurement sensitivity at a given mass loading of the filter 24, extend the measurement range, or modify the cavity 32 resonant characteristics.

In one example, external elements such as screens or meshes, may be placed upstream or downstream of the filter 24, either connected to the housing 32 or exhaust pipes 30, permitting the use of high frequencies above cut-off of the inlet and outlet sections. Alternative to the meshes, it would be possible to provide modifications of the exhaust pipe 30 to prevent transmission of the power down the pipe 30, such as a local narrowing of the exhaust pipe 30, meshes or screens, or even location of other exhaust elements, such as the muffler or the engine. The use of higher frequencies with shorter wavelengths increases the number of resonant modes in the cavity 32, and may improve the spatial resolution of the sensor to measure localized material accumulation or distribution.

The meshes are conducting, and could be connected or disconnected from the side walls of cavity 32 or other conducting elements. Screens are variations of the meshes where the conductors are arranged in a given pattern, without conducting elements in the other directions. Thus, it is possible to affect modes with polarization such that the electric field is parallel to the conductors, but not the other modes. The screens do not necessarily need to be parallel to each other, but they need to have anisotropic properties such that some modes are preferentially affected but not others. The screens can have parallel conducting elements, radial conducting elements, poloidal elements or other patterns. Although the preferred arrangement for the screens and meshes are in planar form, it is not meant to be exclusive to other arrangements.

Additionally, the filter 24 itself may be mounted in a small housing within a larger housing or assembly. This "double-walled" housing structure increases the size of the microwave cavity 32 while concentrating the soot only in the center of the cavity 32 containing the filter 24. Further, the size of the resonant cavity 32 may be increased with respect to the filter 24 such that filter 24 only occupies a small portion of cavity 32, thereby extending the system's operating range.

Figure 4:
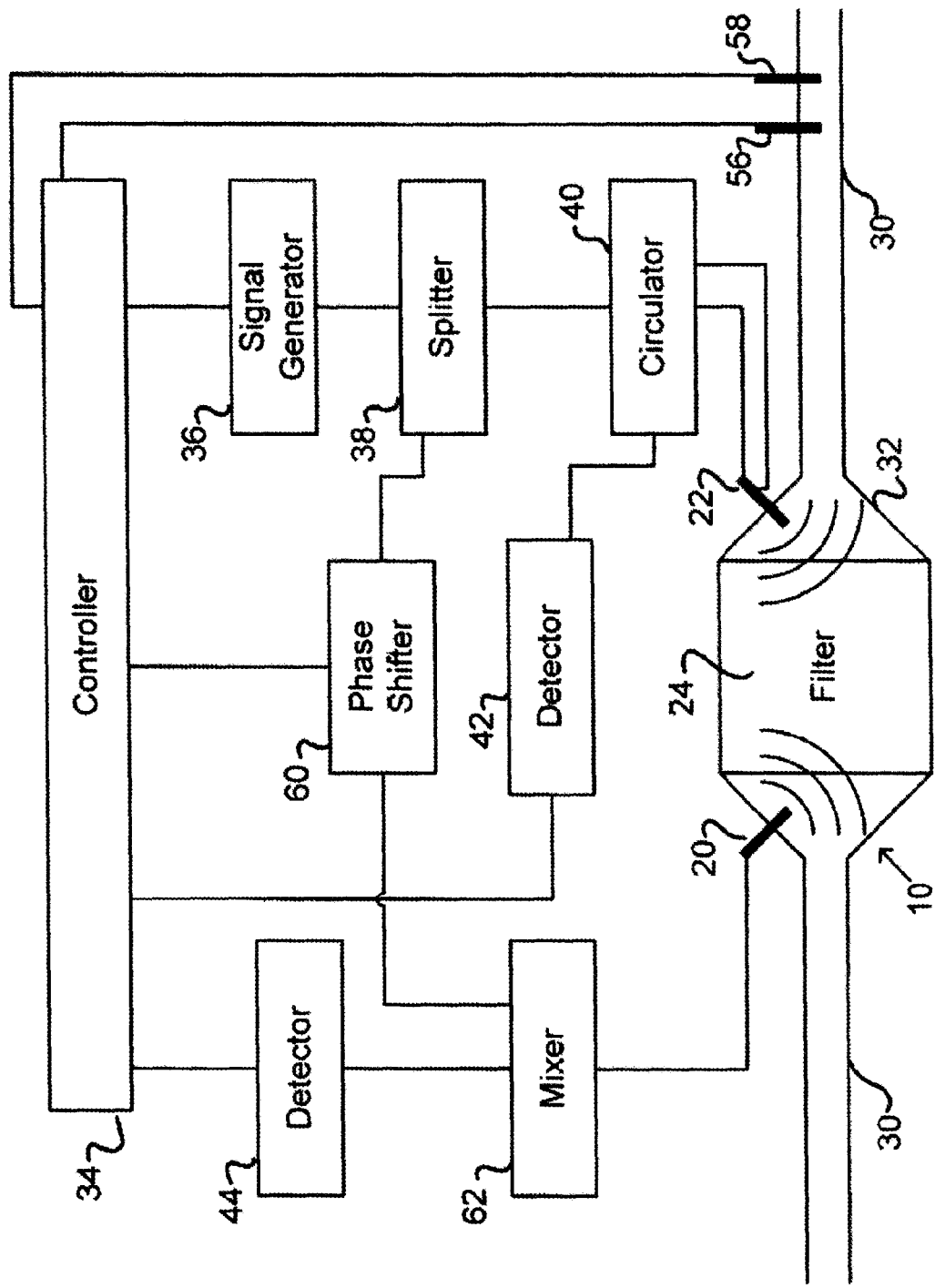
FIG. 4 is an illustration of a microwave filter measurement system according to another embodiment.

FIG. 4 further shows a system using homodyne detection, which may be used to improve the signal-to-noise ratio of the measurement. Controller 34 controls signal generator 36 which feeds the RF signal to splitter 38. Splitter 38 may feed the signal to circulator 40 or phase shifter 60. Phase shifter 60 is connected to mixer 62.

The circulator 40 may be connected to probe 22 permitting and RF signal to be transmitted and received by probe 22 through cavity 32. Alternatively, probe 22 may transmit an RF signal through filter 24 to probe 20. Cavity 32 houses filter 24 and may be connected to conduits 30, comprising a particulate filter unit 10. Cavity 32 may also contain probe 20 connected to mixer 62. Mixer 62 may be connected to detector 44, which is also connected to controller 34. Temperature sensor 56 and moisture sensor 58 may also be connected to conduit 30, either upstream or downstream of filter 24.

The signal received by detectors 42 and 44 may or may not be filtered or amplified before being sent to controller 34.

The system operation utilizes a phase shifter 60 in conjunction with a mixer 62. The phase shifter 60 changes the phase of the signal produced by signal generator 36 and received from splitter 38. The signal from the splitter 38 that goes to the phase shifter 60, (V1) and the signal transmitted through filter 24 housed in cavity 32, (V2) are combined in the mixer 62.

The signal from the mixer 62 has a DC bias, and a component that varies as V1 * V2 * sin (Φ)+DC bias, where Φ is the phase from the phase shifter 60, plus a steady state phase component. The DC bias is independent of Φ. By changing the phase, Φ varies, and the element V1*V2 can be extracted from the signal. By using a larger V1, it is possible to detect small signals from the cavity, V2. The component V1 * V2 * sin (Φ) can be determined through electrically filtering the mixer 62 output or signal processing by the controller 34.

Figure 5:
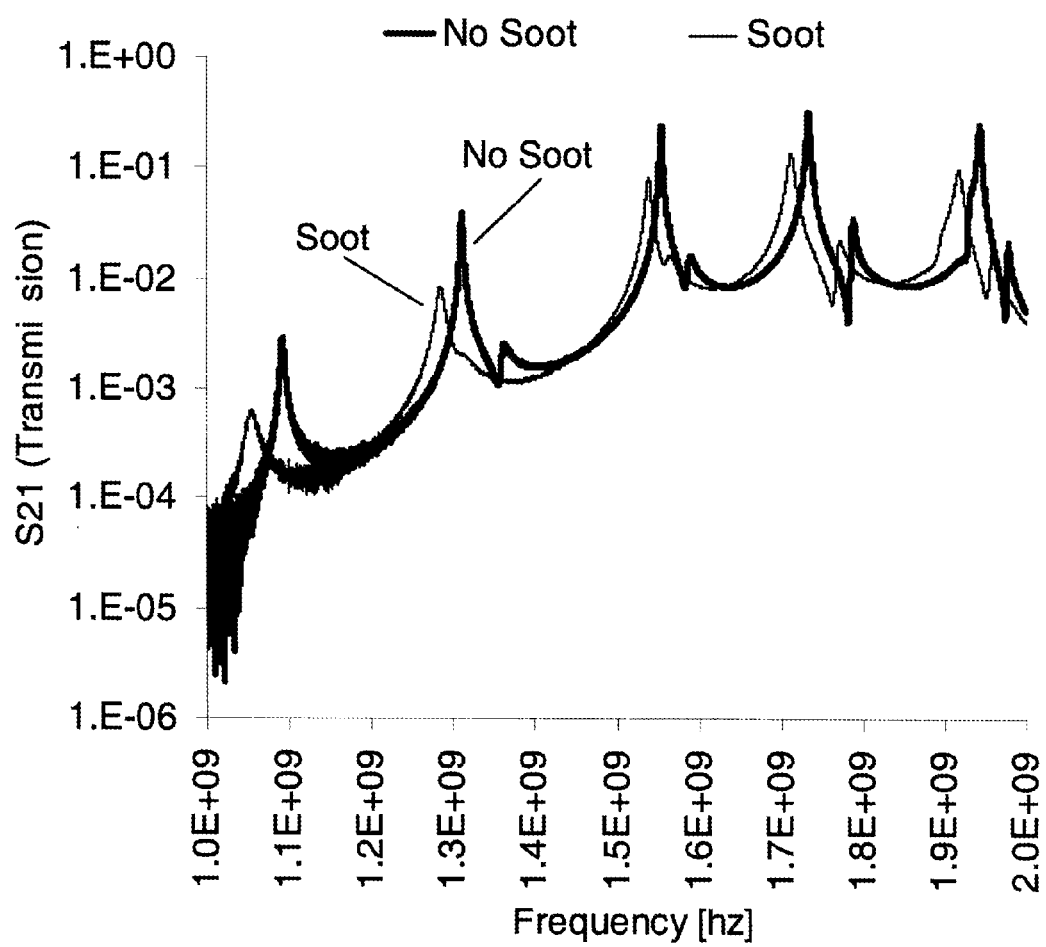
FIG. 5 is a graph of experimentally determined S21 transmission as a function of frequency.
Figure 6:
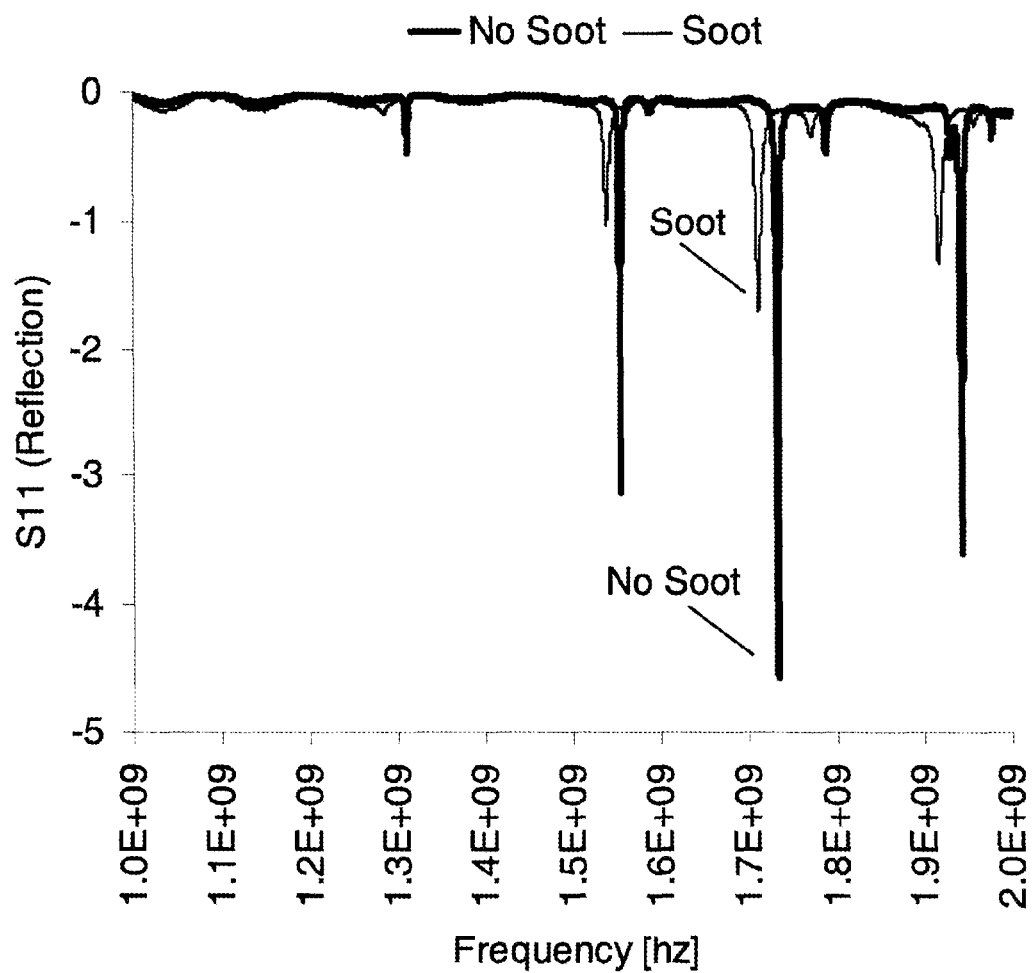
FIG. 6 is a graph of experimentally determined S11 (reflection) response as a function of frequency.

FIG. 5 shows the transmission element S21 as a function of frequency and FIG. 6 shows the reflections from a single launcher/receiver system. In FIG. 5, rod antennas were placed on opposite sides of the trap, as shown in FIG. 1. The graph in FIG. 6 was created with a single antenna and the information is in the reflected signal. Both FIG. 5 and FIG. 6 show multiple resonant modes generated using a voltage controlled oscillator to sweep a frequency range from 1 GHz to 2 GHz and a Schottky diode to detect the transmitted signal in a 5.66 inch diameter cavity containing a cordierite particulate filter. Relative to a clean filter 24, soot accumulation causes a reduction in amplitude of the resonance peaks, a shift in frequency of the resonance peaks, an increase in peak width, and a reduction in quality factor Q. All of these parameters may be used to monitor filter 24 loading, and the changes in signal characteristics are graphically illustrated in FIG. 7.

Specifically, FIG. 5 shows that the presence of soot decreases the resonant frequency at each mode, and also reduces the quality factor, Q. In addition, the amplitude of each peak is also attenuated, as compared to the waveform generated in the absence of soot. Similarly, FIG. 6 shows a dramatic decrease in the amplitude at each resonant frequency, as well as a frequency shift and decrease in Q.

Figure 7:
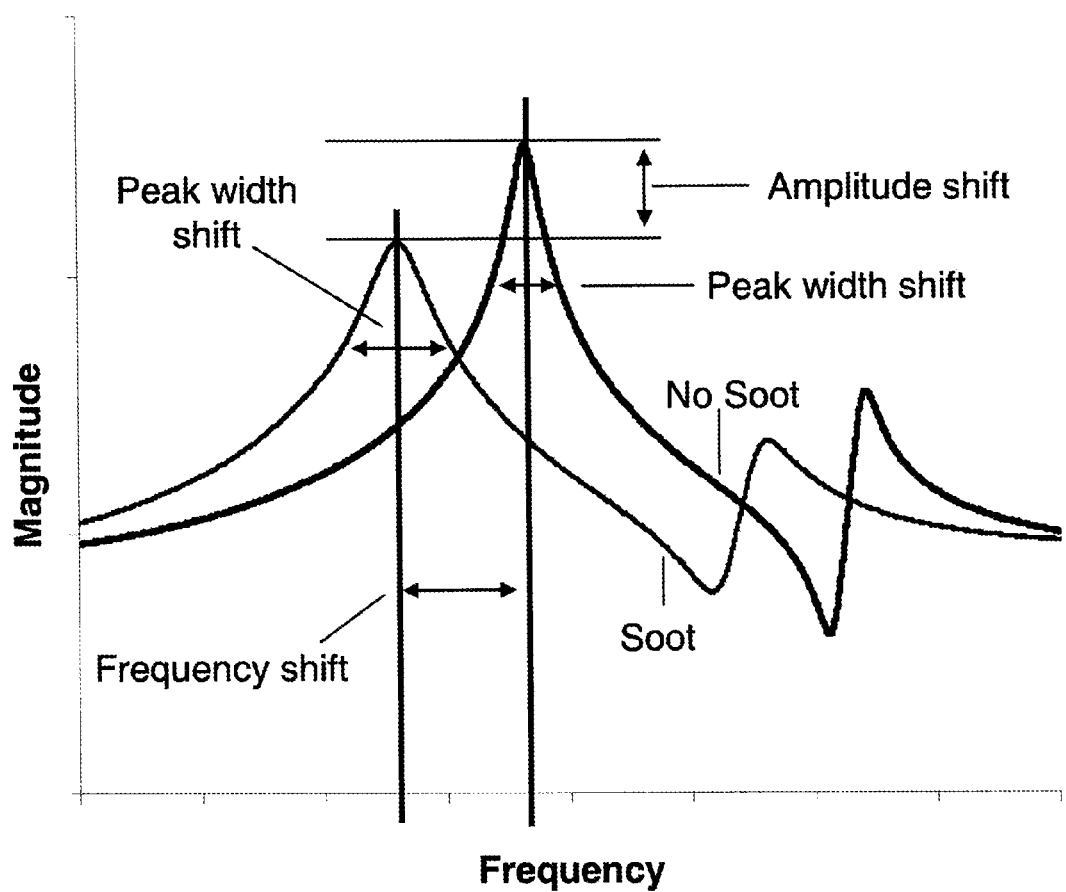
FIG. 7 is a graph showing an expanded view of the transmission mode of FIG. 5.

FIG. 7 is an expanded view of the transmission mode from FIG. 5 and shows detail around the mode near 1.7 GHz. As explained above, the presence of soot changes the characteristics of the received waveform. In this figure, the amplitude is decreased in the presence of soot. Similarly, the peak width is increased, reducing its quality factor, Q. Finally, the frequency of the resonance is shifted, due to the presence of soot. It is these differences that allow a determination of trap loading to be determined.

The signal parameters described above: amplitude, frequency, peak width, quality factor, and the like, including the satellite signals from degenerated modes, may be computed from the sampled resonance curves using controller 34. In some cases, these signal parameters may be determined by analog means and in other cases more advanced signal processing, such as by digital means, and the application of various algorithms may be employed. The algorithms may be stored on a computer readable storage medium in or accessible to controller 34. The resonance curves may be sampled more than once and the signal parameters computed after averaging the resonance curves or multiple cycles, with one cycle being the full frequency range generated by the signal generator 36. In another example, the signal parameters for the resonance curves may be computed for each cycle. Additional signal statistics such as the mean, median, mode, and standard deviation of the various parameters may also computed and utilized to determine filter 24 loading.

Figure 8:
FIG. 8 is a graph showing sensor output as a function of filter soot load.

FIG. 8 shows the sensor output for the microwave sensing system as a function of filter 24 soot load for one cavity 32 resonant mode. In this example, sensor output is the inverse of the signal quality factor. Any of the above mentioned signal parameters may be used to determine filter 24 loading such as amplitude, frequency, peak width, quality factor, and others, with some parameters being more advantageous than others in specific applications. For example, in some cases, signal amplitude may decay in a non-linear fashion with increased filter 24 soot loading while the inverse of signal quality factor may behave linearly, as shown in FIG. 8.

FIG. 8 also depicts a calibration curve which may be uploaded onto a computer readable storage medium accessible by controller 34. The calibration may be in the form of a look-up table, equation, or other suitable form, for example. Comparison of the measured resonance curves and computed parameters may be compared with the calibration values to determine filter 24 loading. In some cases, only one calibration or threshold value may be required, as it may only be important to determine whether or not the filter 24 loading has exceeded some critical value. In other applications, a more detailed calibration function such as that shown in FIG. 8 may be required.

The various resonant modes depicted in FIG. 5 and FIG. 6 are due to variations in the electric field strength in different regions of the cavity 32. Regions of high electric field strength are affected more strongly by the presence of material accumulation in those regions. This effect may be utilized to monitor the distribution of material accumulated in the filter 24.

Figure 9:
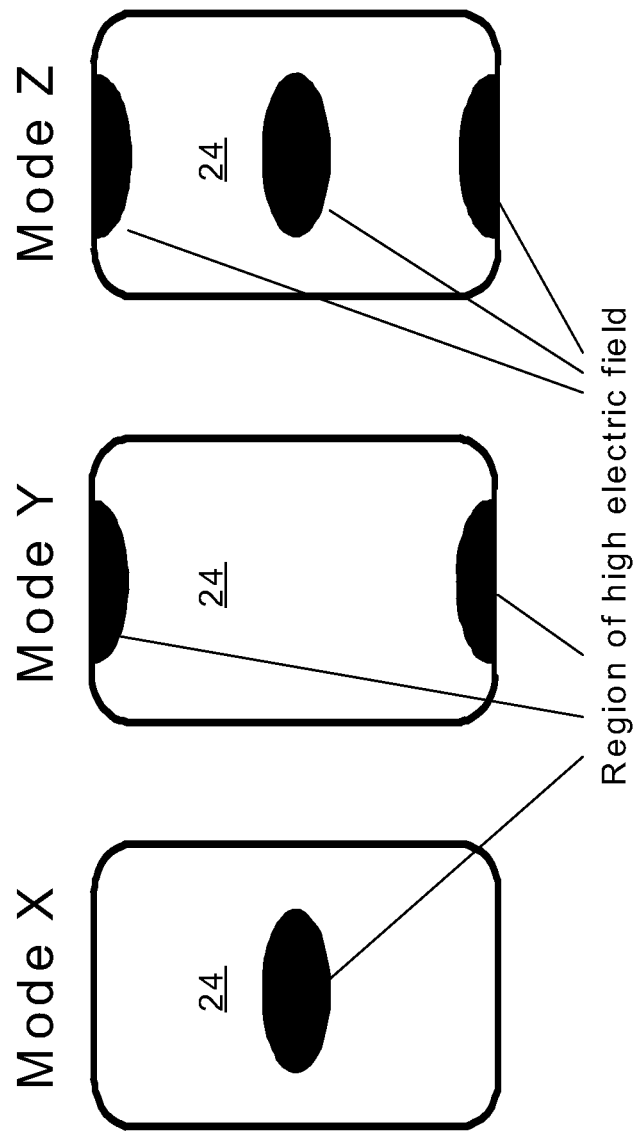
FIG. 9 is an illustration showing how different resonant modes result in different regions of high electric field strength in the filter.

FIG. 9 presents an illustration showing how different resonant modes result in different regions of high electric field strength in filter 24. Only filter 24, and not resonant cavity 32, is shown in FIG. 9. The figure shows mode X resulting in a region of high electric field in the center of filter 24, whereas mode Y results in regions of high electric fields at the inlet and outlet sections of the filter 24. By sampling modes X and Y, the axial distribution of the material loading in filter 24 may be determined. Further increasing the number of modes generated in the filter 24, such as by extending the frequency range of operation, may increase the spatial resolution of the measurement by sampling more regions of the filter 24, as shown by mode Z in FIG. 9. While examples of the axial profile of the modes were shown in FIG. 9, differences in the mode structure and electric field intensities in the radial direction may also exist and can be used to determine the radial distribution of the accumulated material in filter 24.

Figure 10:
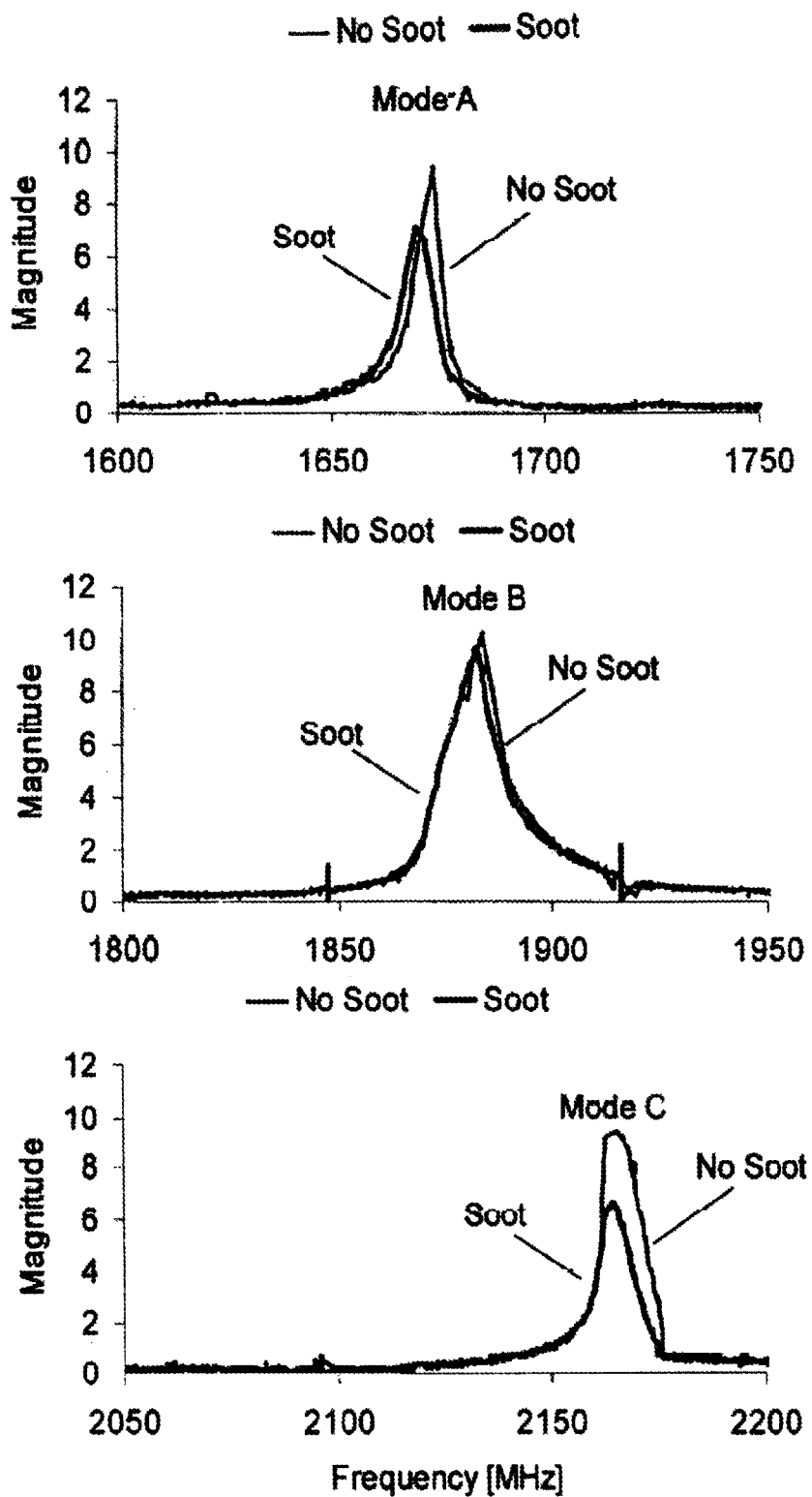
FIG. 10 is a graph showing the response of multiple filter resonant modes to uneven soot distribution.

When the material accumulation in the filter 24 is uniform, all resonant modes may be equally affected. When non-uniformities in the material distribution exist, some modes may be affected more than others. FIG. 10 presents data showing three resonant modes, which are clearly labeled as A, B, and C. The data corresponding to the case without soot is for a clean filter 24. The data corresponding to the case with soot illustrates the effect of non-uniform soot distribution on the resonant mode characteristics. In this case, soot was only deposited near the outer edge of the front face of the filter 24. Clearly modes A and C are affected by the presence of soot in this region of the filter 24, whereas mode B is not.

In one example, multiple resonant modes may be generated in the filter 24 and sampled. A number of signal parameters may be measured or computed from the resonance curve. For each measured signal parameter, $P_{i,m}$, where the subscript "i" corresponds to the mode number, the deviation, $Dev_i$, of the measured signal parameter from the reference signal parameter, $P_{i,r}$, is:

$$Dev_i = (P_{i,m} - P_{i,r})/P_{i,r}.$$

If the deviation, $Dev_i$, of the same signal parameter for each mode, i, is similar, then the filter 24 loading may be uniform. However, if the deviation of the same signal parameter for one mode is significantly different from that of one or more modes the soot loading may be non-uniform.

Application of this example to FIG. 10 for peak amplitude shows $Dev_A$ is −0.24, $Dev_B$ is −0.06, $Dev_C$ is −0.26. The results indicate soot accumulation at front of the filter 24 primarily affects modes A and C, whereas mode B is relatively unaffected. On the other hand, large changes in the signal deviation of mode B relative to modes A and C would indicate little material accumulation at the front of the filter 24. It should be noted however, that the resonant mode structure is a function of the cavity 32 design and geometry. Selection of system operating frequencies to generate the appropriate resonant modes, depends both on cavity 32 geometry as well as the regions of the filter 24 to be sampled. The methods described above can be used to develop the correlations required to related specific resonant modes to material accumulation in different regions of the filter 24.

Figure 11:
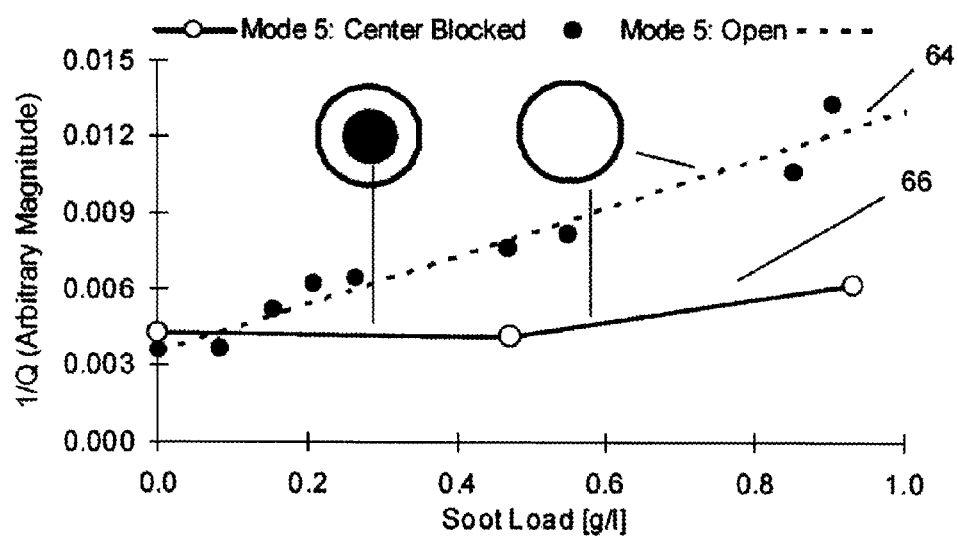
FIG. 11 is a graph showing the sensor output as a function of filter soot load and for different filter soot distributions.

FIG. 11 further illustrates the effect of the spatial distribution of the material accumulated in the filter 24 on the microwave signal response for one filter 24 resonant mode. The graph in FIG. 11 shows the change in the inverse of signal quality factor as a function of filter 24 soot load, for relatively low levels of filter 24 loading. The data corresponding to line 64 resulted from uniform soot accumulation in the filter 24. In line 66, the center of the filter 24 was initially obstructed for the first 0.5 g/L of filter 24 soot loading, thereby preventing soot from depositing in this region of the filter 24.

When no soot was deposited in the center of the filter 24, the resonant mode signal characteristics did not change. Specifically, the data shown in FIG. 11, line 66, shows no change in the inverse of the signal quality factor for filter 24 soot levels from 0 g/L to 0.5 g/L. When the obstruction was removed and soot was deposited in the center of the filter 24, the inverse of the signal quality factor increases with soot loading, also shown by line 66 for soot levels above 0.5 g/L. It should be noted that the signal parameter need not be quality factor as shown in FIG. 11, but can be any suitable parameter such as amplitude, peak width, or frequency of one or more resonant modes, for example. Similarly a signal statistic, such as the mean, median, mode, or standard deviation of one of the signal parameters listed above, may also be used.

In one example, by monitoring the change in one particular mode, such as mode 5, relative to the other resonant modes, the amount of material accumulated in the center of filter 24 may be determined. Similar changes in all of the resonant modes indicate uniform material accumulation within the filter 24, or at least for the regions sampled by the modes used. An increase in the inverse of signal quality factor for mode 5, relative to the other modes, would indicate an increase in the amount of material accumulated in the center of the filter 24. A decrease in the inverse of signal quality factor for mode 5, relative to the other modes, would indicate less material accumulated in the center of the filter 24.

It should be noted however, that any signal parameters or statistics may be used, and that the resonant mode structure is a function of the cavity 32 design and geometry. Selection of system operating frequencies to generate the appropriate resonant modes, depends both on cavity 32 geometry as well as the regions of the filter 24 to be sampled. The inclusion of additional modes, both low and high order, may enhance the spatial resolution of the measurement. Similar correlations relating material loading in various regions of the filter 24 to changes in the characteristics of other resonance modes may be developed.

As illustrated in FIG. 10 and FIG. 11, sampling the resonance curves and comparing the changes in the signal response for multiple resonant modes thus provides information on the spatial distribution of the material accumulated in the filter 24.

In some cases, the location of the material in the filter 24 may not be important, and it may only be important to determine whether or not significant non-uniformities of filter 24 loading exist. In these applications, controller 34 may be configured to initiate an action when the value of at least one signal parameter corresponding to one resonant mode is outside an allowable range. For example, filter 24 regeneration may be initiated when the local filter 24 soot load exceeds some threshold value, and it may not be important where, in filter 24, the higher soot load exists, only that the loading is sufficiently non-uniform, such as to be outside of an acceptable range.

Figure 12:
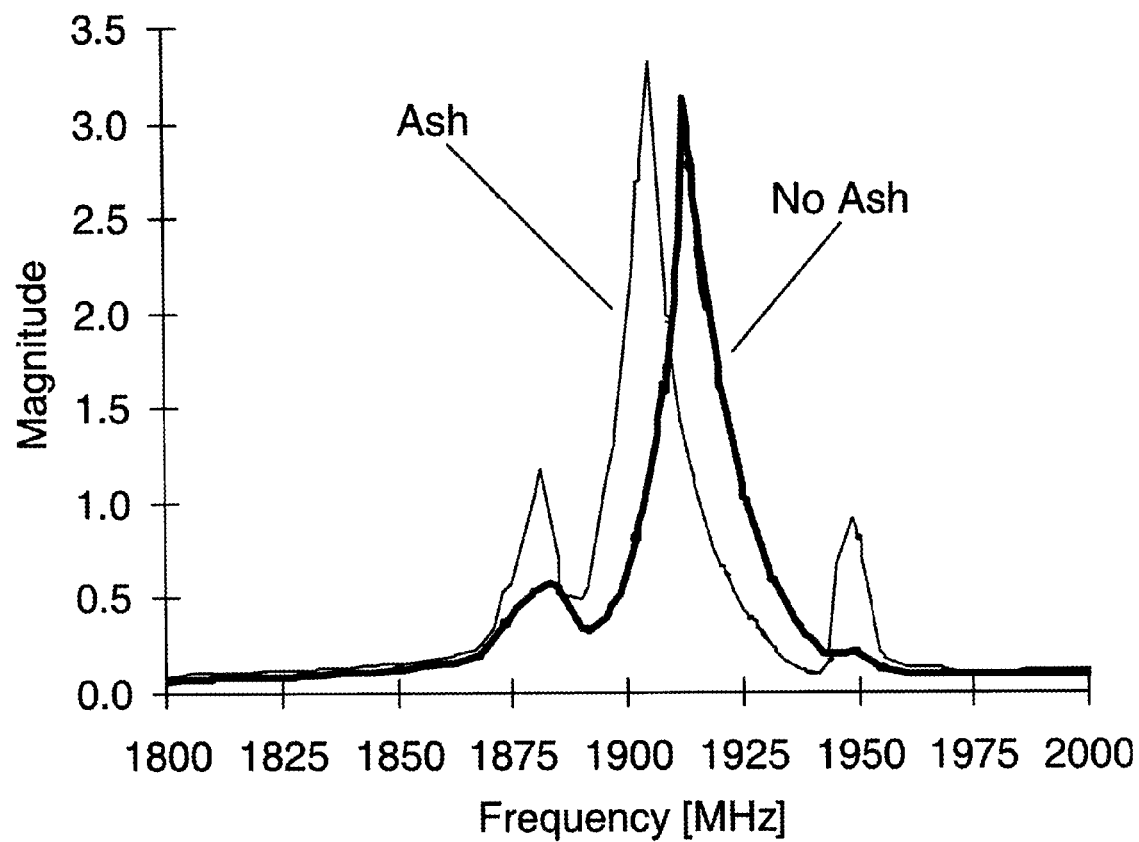
FIG. 12 is a graph showing the response of the microwave signal to ash accumulation in the filter.

The microwave sensing system may also be utilized to determine the type of material accumulated in the filter 24. FIG. 12 illustrates differences in signal characteristics for one filter 24 resonant mode for the cases in which the filter 24 does and does not contain ash. In this example, the presence of the ash strongly affects the degenerate modes, or the small side modes or peaks near the primary resonant modes. As the ash levels in the filter 24 increase, the amplitude, peak width, quality factor, and frequency of these side modes are affected. Monitoring the microwave signal to detect changes in the characteristics of these side modes or peaks provides one means for simultaneously detecting both ash and soot loading.

When conducting particles are deposited in the cavity 32, the dielectric properties of the cavity 32 may change, as there is a partially conducting layer. When this happens, not only does the absorption increase, but the mode properties also vary. This is due to the behavior of the mode under the presence of conducting media on the surface of the filter 24. In general, the modes have different orientation with respect to the surface. Multiple modes at the same frequency exist (degenerate modes), if nothing else because the antennas can generate multiple modes with the same field structure but with different poloidal orientation. A mode with an electric field mainly perpendicular to one of the surfaces (and thus, since the filters usually use square channels), parallel to one of the surfaces, would have different behavior from one where the electric field is at 45 degrees with respect to either surface. Thus, with partially conducting electrical paths, it may be possible to distinguish between the two modes by shifts in frequency. To best use this property, it would be useful to have antennas that can generate multiple modes, (either large antennas), or to have multiple antennas. These antennas could be electrical dipoles (rods), or magnetic dipoles (current loops).

Another type of mode degeneracy would be for modes that are not symmetric with respect to the midplane of the device (the plane perpendicular to the axis half-way from the ends). One mode would have high electric field in on section of the device (may be one end of the device), and low field on the other. Because of symmetry, such a mode would have a corresponding mode with the opposite behavior, with high field on the opposite side. Because of symmetry, both modes would have the same frequency and the same Q for uniformly loaded filter 24. If the contaminant material, ash for example, accumulates in a non-uniform manner, one of the modes would be affected differently from the other, and thus there will be a shift in frequency and a change in Q for one of the modes that is different from the other. Thus, the mode degeneracy is destroyed, and multiple peaks are observed in the measurement.

Two or more antennas or waveguides may be used to transmit the signal through the DPF. For a DPF with non-uniformities, such as non-uniform material loading, using different polarizations (with respect to the DPF) will separate the degenerate modes.

The appearance and disappearance (merging) of peaks could be used to measure the amount and type of material loading, non-uniformity of loading, and other properties of the cavity 32. It may also be possible to measure temperature, which would be useful for characterizing regeneration and to determine soot buildup during normal operation in catalyzed DPFs (where buildup/oxidation depends on the temperature/oxygen/loading characteristics of the trap).

Additionally, ash, which is primarily composed of various metal oxides, sulfates, and phosphates, may also exhibit different dielectric properties from the filter 24 and the soot collected on the filter 24. The dielectric properties of the ash and soot may also vary as a function of temperature and the frequencies used to generate the various resonant modes. In one example the dielectric properties of the ash may result in increased RF signal absorption at elevated temperatures, resulting in a decrease in the amplitude and quality factor (increase in peak width) of one or more resonant modes. In this manner, the ash may be readily detected following high temperature filter 24 regeneration, by comparing the resonant mode characteristics for an ash loaded filter 24 at an elevated temperature to a reference signal for the filter 24 at the same temperature containing no ash. Further, by generating and sampling multiple resonant modes, the distribution of the ash within the filter 24 may be determined.

In general, the amount and distribution of more than one type of material, with each material having different dielectric properties, in a filter 24 may be determined using the methods described above. Further, the dielectric constant of different materials may also have different temperature and frequency dependencies. All of these differences will affect the resonant mode structure and can be utilized to determine both the amount and type of material in the filter 24. These principles can be applied to numerous materials and are not limited to soot or ash.

Additional parameters for determining composition of the accumulated material may be provided by operating the RF filter load measurement system in reflection (S11, S22) and transmission (S12, S21) modes, thereby including additional elements in the coupling matrix.

For any given mode m, the signal amplitude ratio ($A_m$), resonant frequency ($f_m$) and quality factor ($Q_m$) are functions of the loadings of the different species in the filter 24. Thus, $$a_m = F_m(\alpha_1, \alpha_2, \ldots, \alpha_n)$$

$$f_m = G_m(\alpha_1, \alpha_2, \ldots, \alpha_n)$$

$$Q_m = H_m(\alpha_1, \alpha_2, \ldots, \alpha_n)$$

where ($\alpha_1, \alpha_2, \ldots, \alpha_n$) are the loadings of species 1, 2, ..., n. The dependence of the different quantities of $A_m$, $f_m$, and $Q_m$ have different functional dependences on different species, as different species in general have different values of real and imaginary parts of the dielectric constant (the frequency shift is mostly dependent on the real part of the dielectric constant, the amplitude ratio and quality factor more dependent on the imaginary part), and the real and imaginary part also vary with frequency. It is possible through standard means, such as using an expert system, to provide approximations of the content of the different species. External calibration may be required for the inversion algorithm. The larger the number of signals, and the smaller the number of species, the better the estimate is. It is possible to use other diagnostics on-board in conjunction with this method to improve the estimate of the composition.

The inversion algorithms are in the form:

$$\alpha_1 = X(A_1, A_2 \ldots, A_p, f_1, f_2, \ldots, f_p, Q_1, Q_2, \ldots, Q_p)$$

$$\alpha_2 = \Psi(A_1, A_2 \ldots, A_p, f_1, f_2, \ldots, f_p, Q_1, Q_2, \ldots, Q_p)$$

$$\ldots$$

$$\alpha_n = Z(A_1, A_2 \ldots, A_p, f_1, f_2, \ldots, f_p, Q_1, Q_2, \ldots, Q_p)$$

The algorithm can also provide estimates of the deviation from the prediction and the actual loading. As shown in FIGS. 8 and 11, loading is inversely proportional to Q, in one example, although other parameters such as the amplitude, frequency, or width of one or more resonant modes may also be used. Thus, the form of the equation can be instead $$\alpha_1 = X(A_1, A_2 \ldots, A_p, f_1, f_2, \ldots, f_p, 1/Q_1, 1/Q_2, \ldots, 1/Q_p)$$

$$\alpha_2 = \Psi(A_1, A_2 \ldots, A_p, f_1, f_2, \ldots, f_p, 1/Q_1, 1/Q_2, \ldots, 1/Q_p)$$

-continued $$\alpha_n = Z(A_1, A_2, \ldots, A_p, f_1, f_2, \ldots, f_p, 1/Q_1, 1/Q_2, \ldots, 1/Q_p)$$

Furthermore, it is advantageous to determine the dependence of the cavity factor of each mode by equations in the form:

$$A_m = F_m(\alpha_1, \alpha_2, \ldots, \alpha_n)$$

$$f_m = G_m(\alpha_1, \alpha_2, \ldots, \alpha_n)$$

$$1/Q_m = H'_m(\alpha_1, \alpha_2, \ldots, \alpha_n)$$

Inversion of this matrix of algorithm would be more robust than inverting the set of equations using $H_m$.

The process described above can be generalized to include determination of composition distribution. Assuming that $(\alpha_1, \alpha_2, \ldots, \alpha_n)$ are the concentrations that are mostly affected by mode $\alpha$, $(13_1, (\beta_1, \beta_2, \ldots, \beta_n)$ are the concentrations that are mostly detected by mode $\beta$, and so on, the methodology described above can be generalized to include distribution of the different species. "Mostly detected" indicates those regions in the filter 24 where the electric fields of the associated mode are high.

In this case, the inversion algorithm would look like:

$$A_m = F^*_m(\alpha_1, \alpha_2, \ldots, \alpha_n, \beta_1\beta_2, \ldots, \beta_n, \ldots,)$$

$$f_m = G^*_m(\alpha_1, \alpha_2, \ldots, \alpha_n, \beta_1, \beta_2, \ldots, \beta_n, \ldots,)$$

$$1/Q_m = H^*_m(\alpha_1, \alpha_2, \ldots, \alpha_n, \beta_1, \beta_2, \ldots, \beta_n, \ldots,)$$

It is possible that there are more variable than equations, and thus in order to provide the inversion, it may be necessary to make assumptions as to the likely location of the different compounds. The best method would be to build a large matrix of data with different loading of different compounds in different locations, and then use an expert system to derive an inversion algorithm or algorithms.

Figure 13:
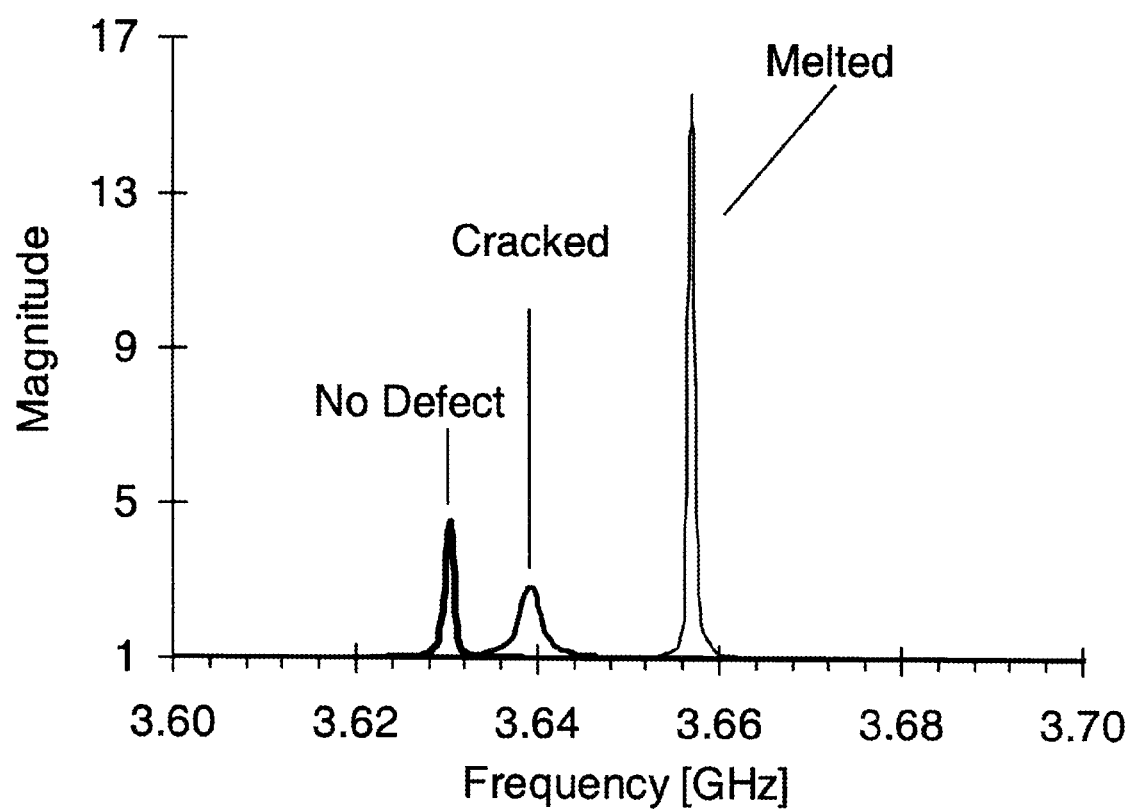
FIG. 13 is a graph showing the response of the microwave signal to filter failures.

Filter 24 failures such as cracking and melting, for example, affect the dielectric properties of the ceramic substrate. Loss of a portion of the substrate via cracking, breakage, or melting creates void spaces in certain regions of the filter 24. Experimental data has shown changes in microwave signal response to filters with various defects, as presented in FIG. 13. The changes in the signal response include a shift in frequency, change in amplitude, and change in filter 24 quality factor, among others.

Additionally, filter 24 failures may be detected by monitoring anomalous material accumulation, or lack thereof, in certain regions of the filter 24. Cracked, broken, or melted filters 24 may allow soot to leak from the filter 24, resulting in regions near the failure with little soot or ash accumulation. Additionally, filter 24 failure modes may also affect the flow of exhaust gases through the filter 24. Changes in the exhaust flow distribution will also affect the deposition profile of the material trapped in the DPF, which can be detected by monitoring the distribution of the accumulated material using multiple resonant modes.

The microwave sensing system disclosed herein can use inexpensive components with the microwave source being a modified microwave chip such as those used in cell phones, and the receiver can be a simple diode with or without amplification. The microwave chip may contain a detector 44 or 42, a signal generator 36, and a controller 34. The detection system can use advanced detection systems such as lock-in detection, heterodyne detection, homodyne detection, and others.

Although the loading has been assumed to be of soot or ash (as from an engine), any matter that builds in a substantial amount on the surface of a filter can be measured as long as it has a dielectric constant different from the background filter material (one in the case of air/engine exhaust).

It is recognized that modifications and variations of the invention will occur to those of ordinary skill in the art and it is intended that all such modifications and variations be included within the scope of the appended claims.

Accordingly, the radio-frequency filter load measurement system and methods of controlling the system of the various embodiments described herein can be used to monitor the amount, type, and distribution of material accumulated in a filter, as well as detect filter or system failures. The system may further initiate an action based on the monitored loading state or condition of the filter.

While the above description contains much specificity, this should not be construed as limiting the scope of any embodiment, but as exemplifications of the presently preferred embodiments thereof. Many other ramifications and variations are possible within the teachings of the various embodiments. For example, the radio-frequency load sensor may be applied to any type of filter in any application where knowledge of the amount, type, and distribution of material loading in the filter is important.

Examples of additional applications of the filter load measurement system described herein include air filters for use in HVAC systems and filter bag houses used in industrial applications. The filters need not be connected to an engine, but may be used for a number of purposes. Further, the filter sensing system is not limited to the filtration of particles from gasses, but is equally applicable to liquids.

Thus the scope of the invention should be determined by the appended claims and their legal equivalents, and not by the examples given.

What is claimed is:

1. A method for determining the contaminant material loading of a filter, wherein said contaminant material displaces a media in said filter, said filter contained within a metallic container forming a resonant cavity, wherein said media in said filter has a first dielectric constant and the contaminant material has a second dielectric constant different from said first dielectric constant, the method comprising:
   establishing microwave energy in the resonant cavity that generates multiple cavity resonant modes;
   monitoring changes in the cavity microwave response of at least two of said multiple cavity resonant modes; and
   determining a contaminant material loading of the filter based on the changes in the cavity microwave response of each of at least two of said multiple cavity resonant modes,
   wherein said determining the contaminant material loading of the filter comprises determining a spatial distribution of the contaminant material in the filter.

2. The method of claim 1, wherein a determination of a filter failure or malfunction is determined based on said changes in the microwave cavity response or said material loading.

3. The method of claim 1, wherein said changes in the cavity microwave response comprise changes in Q, or a derivative change thereof, of at least one of said multiple cavity resonant modes.

4. The method of claim 1, wherein said changes in the cavity microwave response comprise changes in amplitude, or a derivative change thereof, of at least one of said multiple cavity resonant modes.

5. The method of claim 1, wherein said changes in the cavity microwave response comprise changes in frequency, or a derivative change thereof, of at least one of said multiple cavity resonant modes.

6. The method of claim 1, further comprising:
determining the region of said filter associated with each resonant mode;
comparing changes in said multiple resonant modes to each other or to a reference; and
determining the regions of material accumulation based on said comparison of said changes.

7. The method of claim 1, further comprising initiation of filter regeneration, based on said material loading.

8. The method of claim 1, further comprising determining the quantity of ash in said filter.

9. The method of claim 1, wherein one antenna is used in reflection mode to transmit microwave energy to said cavity and receive microwave energy from said cavity.

10. The method of claim 1, wherein two antennas are used in transmission mode, with one antenna transmitting microwave energy to said cavity and the other antenna receiving microwave energy from said cavity.

11. The method of claim 10, wherein each of said two antennas are also used in reflection mode, so as to create a coupling matrix based on the transmitting antenna, the receiving antenna and the mode used.

12. A system for determining the contaminant material loading of a filter, wherein said contaminant material displaces a media in said filter, and said contaminant material has a dielectric constant different from a first dielectric constant of said media, comprising:
a metallic container forming a resonant cavity, housing said filter, wherein said filter is positioned in the cavity to remove contaminant material from a flow;
a frequency generator, outputting a signal having a frequency range so as to encompass multiple resonance modes of said cavity;
at least one antenna to transmit said signal from said frequency generator into said cavity;
at least one antenna to receive said transmitted signal from said cavity; and
a controller that compares parameters of said received signal to a reference, and that determines, based on said comparison, said contaminant material loading;
wherein said controller further determines a spatial distribution of the contaminant material loading in the filter.

13. The system of claim 12, wherein said reference comprises a previously received signal.

14. The system of claim 12, wherein said reference comprises a stored value.

15. The system of claim 12, wherein said parameters are selected from the group consisting of amplitude, frequency and quality factor, or a derivative thereof.

16. The system of claim 12, wherein a determination of a filter failure or malfunction is determined based on said parameters or said material loading.

17. A method for determining the contaminant material loading of a filter, wherein said contaminant material displaces a media in said filter, said filter contained within a container forming a resonant cavity, wherein said media has a first dielectric constant and said contaminant material has a second dielectric constant different from said first dielectric constant, the method comprising:
selecting a region of interest for monitoring contaminant material accumulation in the filter located within the cavity;
selecting a frequency range suitable to generate at least one cavity resonant mode corresponding to said region of interest, based on the cavity geometry and dielectric properties;
establishing microwave energy in the cavity over the selected frequency range to establish said at least one cavity resonant mode;
monitoring changes in the cavity microwave response at said at least one cavity resonant mode;
determining contaminant material loading based on the changes in the cavity microwave response at said resonant mode,
wherein said determining contaminant material loading comprises determining local accumulation of the material in said region of interest.

18. The method of claim 17, wherein said changes in the cavity microwave response comprise changes in Q, or a derivative change thereof, of said at least one cavity resonant mode.

19. The method of claim 17, wherein said changes in the cavity microwave response comprise changes in amplitude, or a derivative change thereof, of said at least one cavity resonant mode.

20. The method of claim 17, wherein said changes in the cavity microwave response comprise changes in frequency, or a derivative change thereof, of said at least one cavity resonant mode.

* * * * *